United States Patent
Auld et al.

(10) Patent No.: US 7,566,173 B2
(45) Date of Patent: Jul. 28, 2009

(54) MULTI-SPOT OPHTHALMIC LASER PROBE

(75) Inventors: Jack R. Auld, Laguna Niguel, CA (US); Ronald T. Smith, Newport Coast, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/774,698

(22) Filed: Jul. 9, 2007

(65) Prior Publication Data
US 2009/0015923 A1    Jan. 15, 2009

(51) Int. Cl.
*G02B 6/42* (2006.01)
(52) U.S. Cl. ............................. 383/33; 606/4
(58) Field of Classification Search ............. 250/201.5, 250/559.38; 369/44.11, 44.23, 44.26; 385/147
See application file for complete search history.

(56) References Cited

U.S. PATENT DOCUMENTS

| | | | |
|---|---|---|---|
| 4,062,043 A | | 12/1977 | Zeidler et al. |
| 4,111,524 A | * | 9/1978 | Tomlinson, III ............... 385/37 |
| 4,274,706 A | * | 6/1981 | Tangonan .................... 385/37 |
| 4,679,901 A | * | 7/1987 | Dammann et al. .......... 359/575 |
| 4,865,029 A | * | 9/1989 | Pankratov et al. .............. 606/4 |
| 4,986,262 A | * | 1/1991 | Saito .......................... 600/108 |
| 5,090,400 A | * | 2/1992 | Saito .......................... 600/108 |
| 5,125,922 A | * | 6/1992 | Dwyer et al. ................... 606/3 |
| 5,150,254 A | * | 9/1992 | Saitou ......................... 359/367 |
| 5,261,904 A | * | 11/1993 | Baker et al. .................. 606/17 |
| 5,275,593 A | * | 1/1994 | Easley et al. ................... 606/4 |
| 5,356,407 A | * | 10/1994 | Easley et al. ................... 606/4 |
| 5,373,526 A | * | 12/1994 | Lam et al. ..................... 372/69 |
| 5,396,571 A | | 3/1995 | Saadatmanesh et al. |
| 5,499,137 A | * | 3/1996 | Shiraishi ..................... 359/564 |
| 5,555,129 A | * | 9/1996 | Konno et al. ................. 359/569 |
| 5,630,809 A | * | 5/1997 | Connor .......................... 606/4 |
| 5,659,642 A | * | 8/1997 | King et al. ..................... 385/16 |
| 5,715,089 A | * | 2/1998 | Shiraishi ..................... 359/558 |
| 5,841,912 A | * | 11/1998 | Mueller-Fiedler et al. ..... 385/17 |
| 5,921,981 A | * | 7/1999 | Bahmanyar et al. ............ 606/4 |
| 5,973,779 A | * | 10/1999 | Ansari et al. ................. 356/301 |
| 5,980,454 A | * | 11/1999 | Broome ....................... 600/176 |
| 6,066,128 A | * | 5/2000 | Bahmanyar et al. ............ 606/4 |
| 6,071,748 A | * | 6/2000 | Modlin et al. ................ 436/174 |
| 6,080,143 A | * | 6/2000 | Connor .......................... 606/4 |
| 6,096,028 A | * | 8/2000 | Bahmanyar et al. ............ 606/4 |
| 6,097,025 A | * | 8/2000 | Modlin et al. ........... 250/227.22 |
| 6,241,721 B1 | * | 6/2001 | Cozean et al. .................. 606/6 |
| 6,370,422 B1 | * | 4/2002 | Richards-Kortum et al. 600/478 |
| 6,421,179 B1 | * | 7/2002 | Gutin et al. .................. 359/572 |
| 6,441,934 B1 | * | 8/2002 | Boord et al. ................... 398/87 |
| 6,520,956 B1 | * | 2/2003 | Huang ........................... 606/5 |

(Continued)

FOREIGN PATENT DOCUMENTS

EP    1191359    3/2002

(Continued)

*Primary Examiner*—Frank G Font
*Assistant Examiner*—Peter Radkowski
(74) *Attorney, Agent, or Firm*—Jonathan E. Prejean

(57) ABSTRACT

A laser probe includes an emitting optical fiber, optics, and two or more receiving optical fibers. The emitting optical fiber emits a beam of laser light. The optics diffract the beam of light emitted by the emitting optical fiber. The receiving optical fibers each receive a beam of light diffracted by the optics.

27 Claims, 7 Drawing Sheets

U.S. PATENT DOCUMENTS

| | | | |
|---|---|---|---|
| 6,539,132 B2 * | 3/2003 | Ivtsenkov et al. | 385/7 |
| 6,563,982 B1 * | 5/2003 | Xie et al. | 385/33 |
| 6,687,010 B1 * | 2/2004 | Horii et al. | 356/479 |
| 6,975,898 B2 * | 12/2005 | Seibel | 600/473 |
| 7,071,460 B2 * | 7/2006 | Rush | 250/227.11 |
| 7,231,243 B2 * | 6/2007 | Tearney et al. | 600/407 |
| 7,252,662 B2 * | 8/2007 | McArdle et al. | 606/5 |
| 2001/0055462 A1 * | 12/2001 | Seibel | 385/147 |
| 2002/0013572 A1 * | 1/2002 | Berlin | 606/4 |
| 2002/0054725 A1 * | 5/2002 | Ivtsenkov et al. | 385/7 |
| 2002/0111608 A1 * | 8/2002 | Baerveldt et al. | 606/6 |
| 2003/0020922 A1 * | 1/2003 | Crowley et al. | 356/502 |
| 2003/0081220 A1 * | 5/2003 | Ostrovsky et al. | 356/479 |
| 2004/0012856 A1 * | 1/2004 | Gutin | 359/573 |
| 2004/0109164 A1 * | 6/2004 | Horii et al. | 356/479 |
| 2004/0116909 A1 * | 6/2004 | Neuberger et al. | 606/4 |
| 2004/0195511 A1 * | 10/2004 | Elmore et al. | 250/339.02 |
| 2005/0075704 A1 * | 4/2005 | Tu et al. | 607/88 |
| 2005/0143719 A1 * | 6/2005 | Sink | 606/9 |
| 2005/0154379 A1 * | 7/2005 | McGowan et al. | 606/4 |
| 2005/0197655 A1 * | 9/2005 | Telfair et al. | 606/5 |
| 2005/0240168 A1 * | 10/2005 | Neuberger et al. | 606/4 |
| 2005/0245916 A1 * | 11/2005 | Connor | 606/4 |
| 2006/0013533 A1 * | 1/2006 | Slatkine | 385/31 |
| 2006/0100613 A1 * | 5/2006 | McArdle et al. | 606/4 |
| 2006/0106370 A1 * | 5/2006 | Baerveldt et al. | 606/4 |
| 2006/0114473 A1 * | 6/2006 | Tearney et al. | 356/479 |
| 2006/0195076 A1 * | 8/2006 | Blumenkranz et al. | 606/4 |
| 2007/0057211 A1 * | 3/2007 | Bahlman et al. | 250/584 |
| 2007/0121069 A1 * | 5/2007 | Andersen et al. | 351/221 |
| 2007/0179430 A1 * | 8/2007 | Smith et al. | 604/20 |
| 2007/0238955 A1 * | 10/2007 | Tearney et al. | 600/407 |
| 2007/0265602 A1 * | 11/2007 | Mordaunt et al. | 606/4 |
| 2007/0299430 A1 * | 12/2007 | McArdle et al. | 606/5 |
| 2008/0013960 A1 * | 1/2008 | Tearney et al. | 398/139 |
| 2008/0097225 A1 * | 4/2008 | Tearney et al. | 600/478 |
| 2008/0308730 A1 * | 12/2008 | Vizi et al. | 250/309 |

FOREIGN PATENT DOCUMENTS

| | | |
|---|---|---|
| WO | WO 99/08612 | 2/1999 |
| WO | WO 2006/116141 | 11/2006 |

* cited by examiner

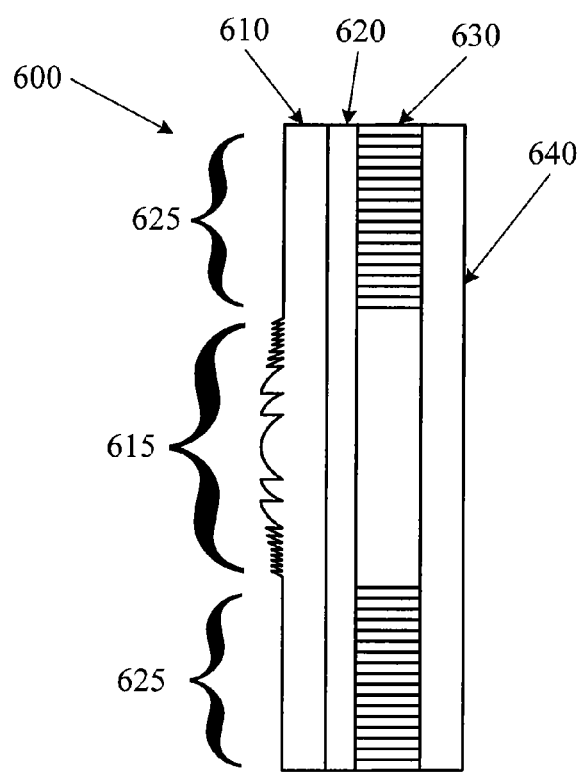
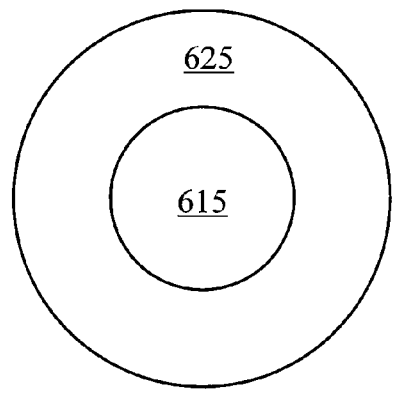
Fig. 6A
Fig. 6B
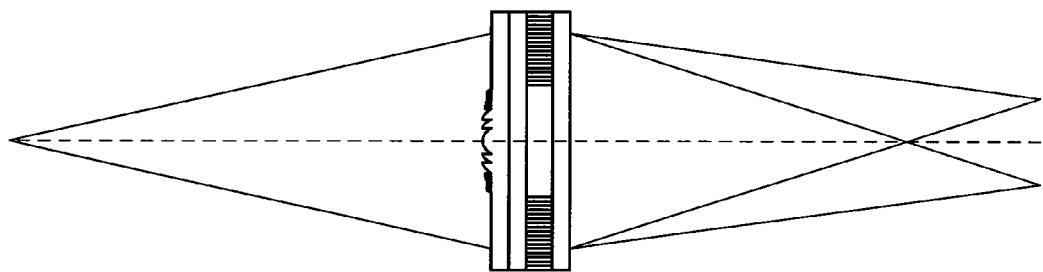
Fig. 7

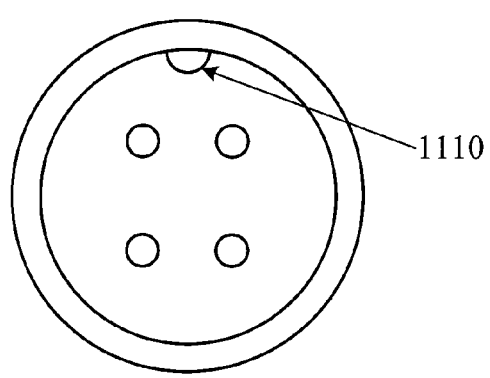
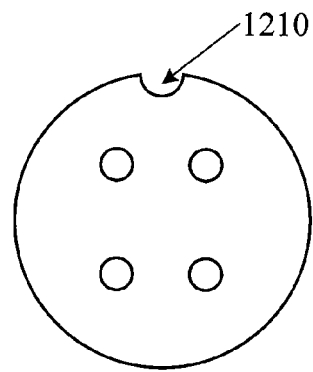
Fig. 11              Fig. 12
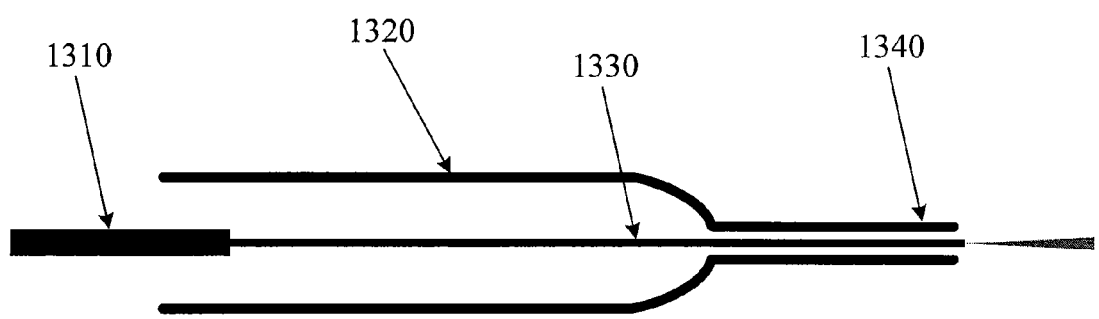
Fig. 13

MULTI-SPOT OPHTHALMIC LASER PROBE

BACKGROUND OF THE INVENTION

The present invention relates to a laser probe for use in ophthalmic procedures and more particularly to a multi-spot laser probe for use in photocoagulation.

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina.

Macular degeneration is a medical condition predominantly found in elderly adults in which the center of the inner lining of the eye, known as the macula area of the retina, suffers thinning, atrophy, and in some cases bleeding. This can result in loss of central vision, which entails inability to see fine details, to read, or to recognize faces. According to the American Academy of Ophthalmology, it is the leading cause of central vision loss and in the United States today for those over the age of fifty.

When blood vessels beneath the retina bleed, a form of macular degeneration, called wet macular degeneration, results. In some cases, this bleeding may be halted or slowed using a procedure known as photocoagulation. Photocoagulation is a technique employed by retinal surgeons to treat a number of eye conditions, one of which is the exudative (wet) form of macular degeneration. In this treatment, laser light rays are directed into the eye focusing on abnormal blood vessels that are growing beneath the retina. This laser cauterizes the vessels to seal them from further leakage in the hope of preventing further vision loss.

Using a standard laser probe with one emitted beam spot, the ophthalmic surgeon typically turns the laser beam off and on in rapid fire succession with a foot pedal as he scans the beam across the retinal surface to create a one-dimensional or two-dimensional array of photocoagulated laser burn spots on the retina. It can take a long time to cover the desired retinal area with photocoagulated spots using a single-beam laser probe.

A multi-spot laser probe can potentially reduce the time required to create the desired pattern of laser burn spots. However, given a laser with limited laser beam power that is already operating at its maximum laser power setting, a multi-spot laser probe may not necessarily reduce the time required to create the desired laser burn spot pattern. This is because the fixed laser power P is divided between N beam spots so the power in a given beam spot is on average only P/N. Therefore, to create an equivalent burn, the required exposure time is roughly N times the exposure time for a single-beam laser probe. Therefore, although there are only 1/N the required number of laser fires from a single beam probe, the exposure time per beam fire is N times that of a single beam probe. So the overall time to lay down the array of burn spots remains the same.

However, there are now available new photocoagulation lasers such as the Alcon Laboratories, Inc.'s NGL (Next Generation Laser) whose desired beam intensity to create an ideal photocoagulation spot is a small fraction f of the maximum available beam intensity. If f is equal to 1/N, then a multi-spot laser beam with N emitted beams can be used with the laser beam at maximum power level and the overall time to create the desired coagulation spot patterns is only 1/N of the time required with the single-spot laser probe. This reduces the overall time for each operation and enables more operations to be performed in a given day, causing the overall cost per operation to be reduced. Therefore, it would be desirable to have a multi-spot laser probe for performing photocoagulation.

SUMMARY OF THE INVENTION

In one embodiment consistent with the principles of the present invention, the present invention is a laser probe comprising an emitting optical fiber, optics, and two or more receiving optical fibers. The emitting optical fiber emits a beam of laser light. The optics diffract the beam of light emitted by the emitting optical fiber. The receiving optical fibers each receive a beam of light diffracted by the optics.

In another embodiment consistent with the principles of the present invention, the present invention is a coupling for a laser probe comprising a housing, optics located in the housing, and two connectors—one located on each side of the optics. The optics diffract a beam of incident light.

In another embodiment consistent with the principles of the present invention, the present invention is an ophthalmic laser probe comprising an emitting optical fiber and optics. The optics diffract the beam of light emitted by the emitting optical fiber into two or more diffracted beams of light.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 6A and 6B are a side cross section view and a front view, respectively, of a hybrid surface grating/volume hologram multiplex grating assembly.

FIG. 7 is a side cross section view of the beam pattern produced by the hybrid surface grating/volume hologram multiplex grating assembly of FIG. 6.

FIGS. 11 and 12 are end views of female and male connectors, respectively, according to the principles of the present invention.

FIG. 13 is a cross section view of a laser probe.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
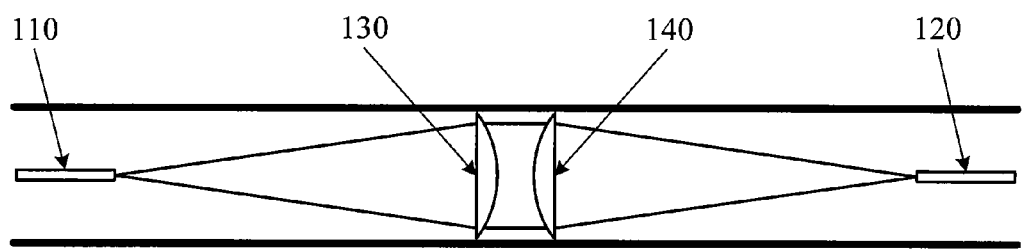
FIG. 1 is cross section view of a simple fiber to fiber imaging system consistent with the principles of the present invention.

FIG. 1 is cross section view of a simple fiber to fiber imaging system consistent with the principles of the present invention. In the embodiment of FIG. 1, the system has two fibers 110, 120, and two lenses 130, 140. Fiber 110 emits a beam of diverging light that originates from a laser source (not shown). The diverging beam is collimated by lens 130. As is commonly known, collimated light is light whose rays are parallel with a planar wave front. This collimated beam is focused by lens 140 into a small diameter spot at the entrance face of receiving fiber 120. In this case, the lenses 130, 140 are each plano-convex aspheric lenses. In a plano-convex aspheric lens, one surface is planar and the other surface is convex with a precise aspheric surface in order to focus the light to a minimum diameter spot. Such an arrangement gives the lowest beam aberrations and can result in a nearly perfect diffraction limited laser spot at the receiving fiber 120.

In one embodiment of the present invention, the fibers 110, 120 are each 50 micron, 0.15 NA fibers. The lenses are appropriately sized to fit inside a standard ophthalmic hand piece with an inner diameter of 0.035 inches such as that manufactured and sold by Alcon Laboratories, Inc.

Figure 2:
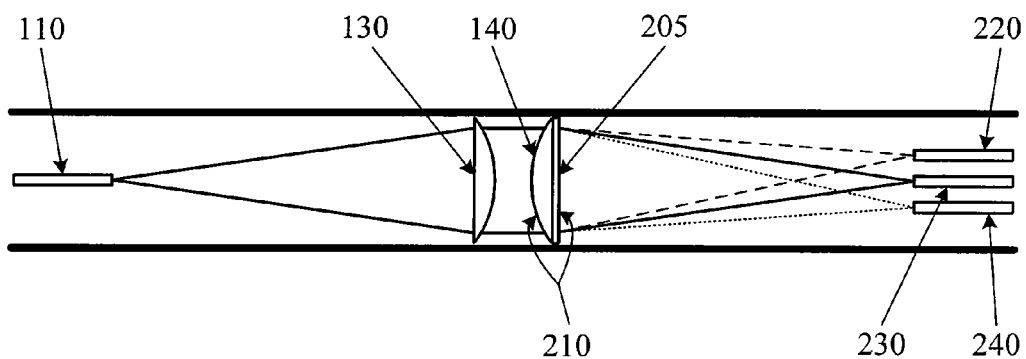
FIG. 2 is a cross section view of a fiber to fiber imaging system using a lens with a diffraction grating consistent with the principles of the present invention.

FIG. 2 is a cross section view of a fiber to fiber imaging system using a lens with a diffraction grating. In FIG. 2, the system includes an emitting fiber 110, a lens 130, a lens 140 with a diffractive grating 205, and three receiving fibers 220, 230, 240. In the embodiment of FIG. 2, a diffractive grating 205 is located on the planar side of the plano-convex lens 140. Such a diffractive grating is capable of diffracting the incident beam into multiple exit beams that focus to individual spots as shown. In this case, lens/grating assembly 210 diffracts the incident beam and focuses it into two different discrete beam spots. The depths of the surface grating features are designed so that about one-third of the light is diffracted into each diffracted spot and one-third of the light remains in the undiffracted zero order spot. In such a case, each of the three receiving fibers 220, 230, 240 carries about one-third of the laser light from the incident beam.

Figure 4:
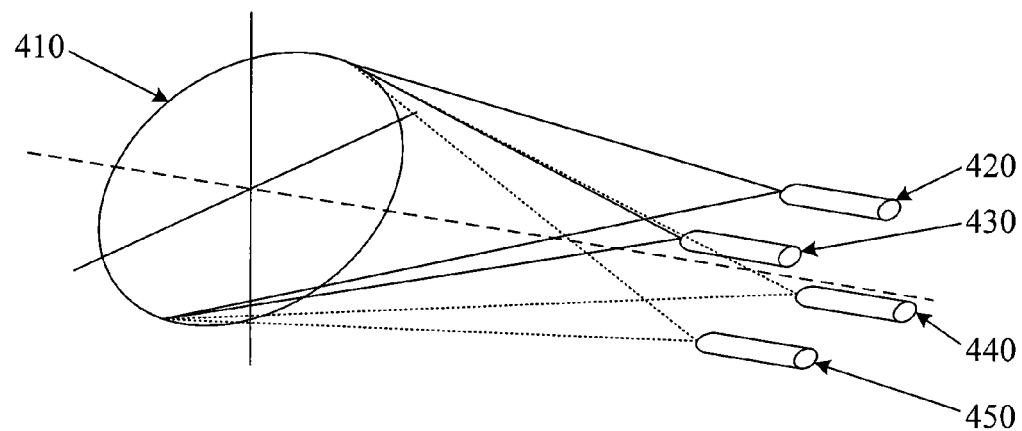
FIG. 4 is a representation of a diffractive grating that produces a 2×2 array of spots according to the principles of the present invention.

Such an arrangement produces multiple laser spots from a single incident laser beam. The diffractive grating 205 on lens/grating assembly 210 can be designed to produce a number of diffracted beam spots which can be coupled to a number of receiving fibers 220, 230, 240. In one example, the diffractive grating can be designed to diffract the incident beam so that nearly 100% of the light is directed into the diffracted beams (and the zero order beam is suppressed). In general, such gratings can be designed to produce a diffractive pattern of beams along a line or in a two-dimensional area (as shown in FIG. 4). The diffractive grating 205 of FIG. 2 can be in direct physical contact with lens 140 or may be separate from it. In such a case, the diffractive grating may be implemented by a polymer or glass structure that is separate from the lens. The diffraction grating 205 that is separate from converging lens 140 can either be located downstream from converging lens 140, between converging lens 140 and collimating lens 130, or upstream from collimating lens 130.

Figure 3:
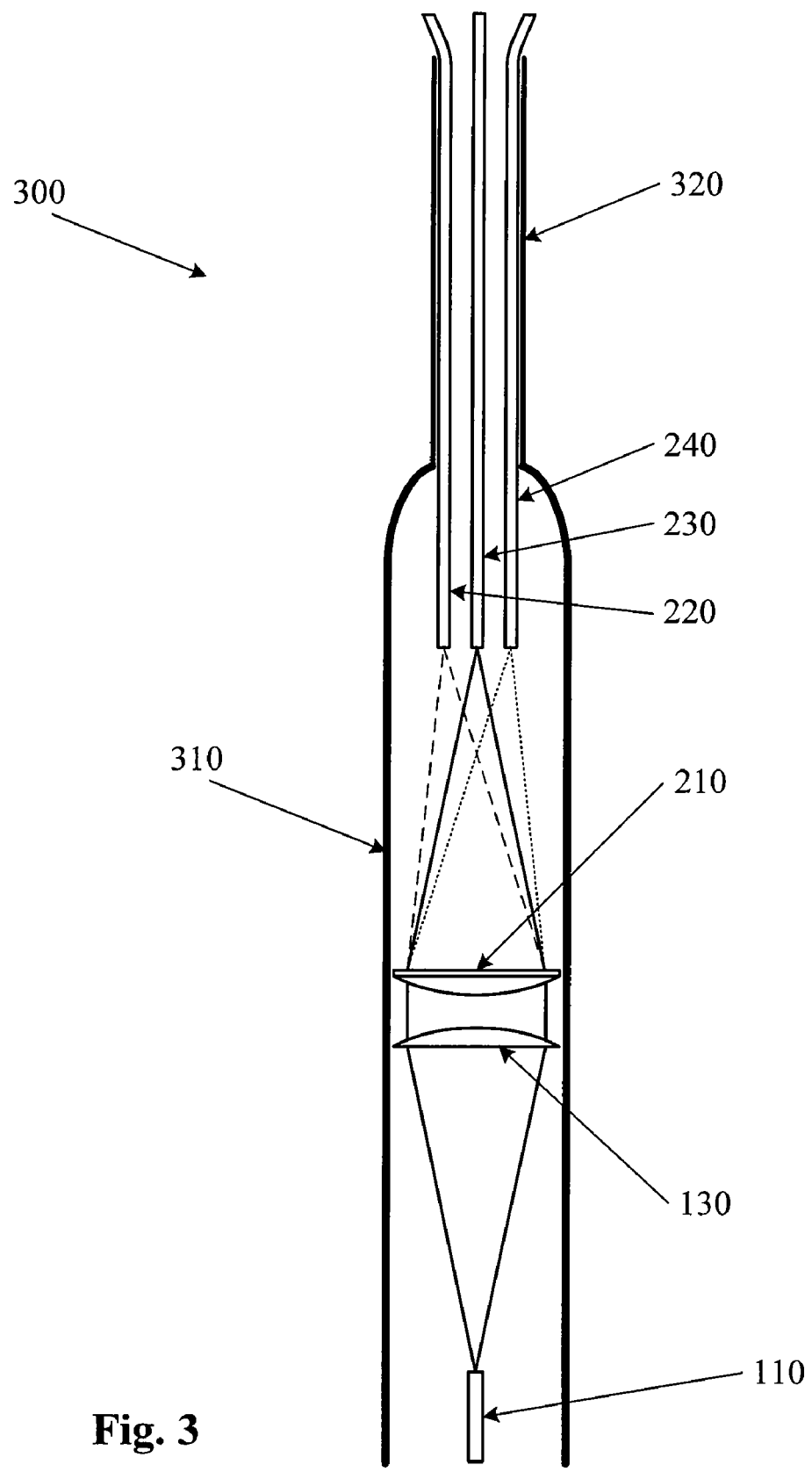
FIG. 3 is a cross section view of a distal end of a laser probe including a hand piece and attached cannula according to the principles of the present invention.

FIG. 3 depicts a distal end of a laser probe including a hand piece and attached cannula according to the principles of the present invention. In FIG. 3, the laser probe assembly 300 includes an emitting fiber 110, a lens 130, a lens with a diffractive grating 210, three receiving fibers 220, 230, 240, a handpiece 310, and a cannula 320. Each of the three receiving fibers 220, 230, 240 has a bent distal end. These bent ends direct the diffracted laser spots to different locations thereby producing a spot pattern. When laser probe assembly 300 is used for photocoagulation of retinal blood vessels, the bent ends of the receiving fibers 220, 230, 240 produce a spot pattern that can be used to more quickly and efficiently coagulate the blood vessels. Each time the laser is fired, multiple spots can be projected onto the retina covering a larger portion of its surface.

FIG. 4 is a representation of a diffractive grating that produces a 2×2 array of spots according to the principles of the present invention. In FIG. 4, diffractive grating 410 produces 4 spots in a two-dimensional area. Each of the four spots is aligned with a receiving fiber 420, 430, 440, 450. Any number of different spot configurations can be implemented by different designs of diffractive grating 41 0.

Figure 5:
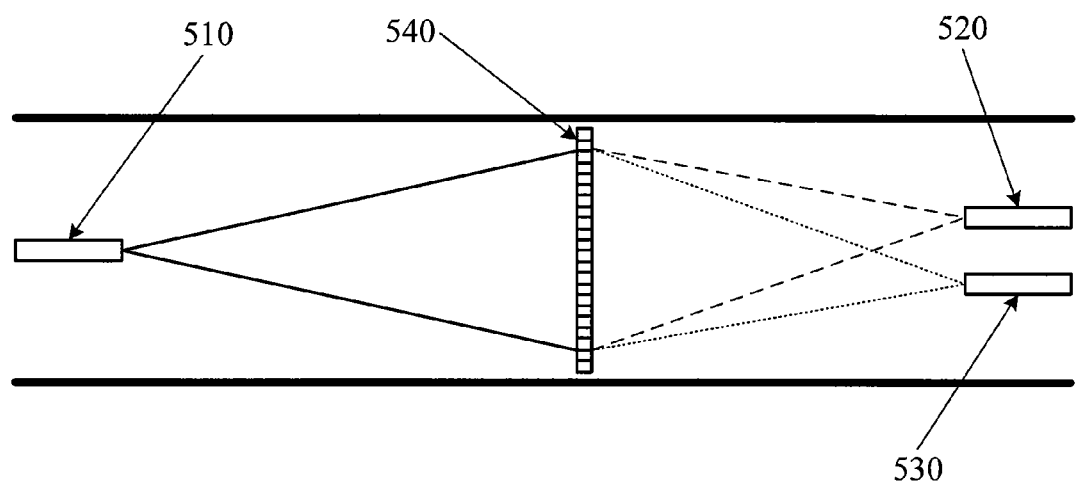
FIG. 5 depicts an imaging system using a diffractive grating according to the principles of the present invention.

FIG. 5 depicts an imaging system using a diffractive grating according to the principles of the present invention. In FIG. 5, the system includes an emitting fiber 510, two receiving fibers 520, 530, and a diffractive grating 540. In FIG. 5, the refractive lenses have been removed and replaced with diffractive grating 540. In this case, at the edge of the grating 540, a bend angle of about 17 degrees is required (for a 1:1 magnification, 0.15 NA optical system). Surface relief gratings are capable of near 100% diffraction efficiency for small bend angles, but as the bend angle increases, the diffraction efficiency tends to drop rapidly. In such a case, a volume hologram can be used as a diffraction grating.

FIGS. 6A and 6B are a side cross section view and a front view, respectively, of a hybrid surface grating/volume hologram multiplex grating assembly. In FIG. 6A, grating assembly 600 includes a surface relief grating layer 610, an adhesive layer 620, a volume hologram layer 630, and a glass substrate 640. The grating assembly 600 has a central (surface grating diffraction) region 615, and a peripheral (volume hologram diffraction) region 625. Grating assembly 600 is generally circular in shape as shown in FIG. 6B.

The peripheral (volume hologram diffraction) region 625 implements a volume hologram. In a volume hologram, the diffraction grating lies inside the bulk volume of the hologram material. A volume hologram has moderate to low diffraction efficiencies for low bend angles (e.g. less than 10 degrees) and potentially 100% diffraction efficiency for higher bend angles (e.g. greater than 10 degrees).

Therefore, the diffraction assembly 600 efficiently diffracts for small bend angles with the central (surface grating diffraction) region 615. The assembly 600 also efficiently diffracts for higher bend angles with the peripheral (volume hologram diffraction) region 625. Using such an assembly 600 can result in near 100% diffraction efficiency in a constrained volume contained in a hand piece or probe. An exemplary beam pattern for grating assembly 600 is shown in FIG. 7.

Figure 8:
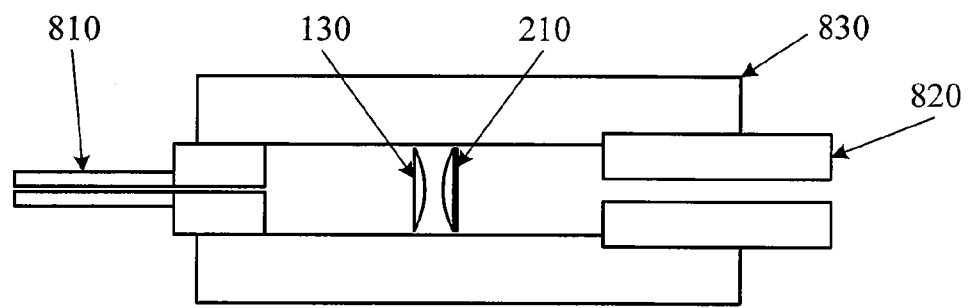
FIG. 8 is a cross section view of a coupling arrangement according to the principles of the present invention.
Figure 9:
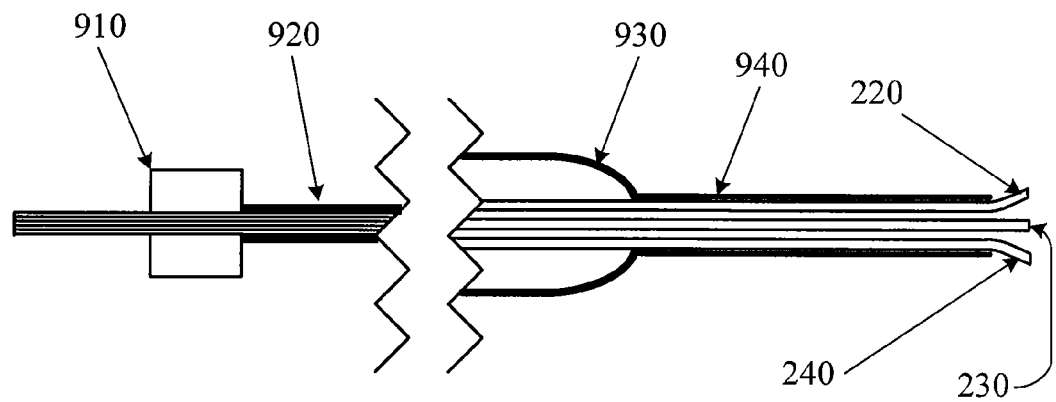
FIG. 9 is a partial view of a laser probe according to the principles of the present invention.
Figure 10:
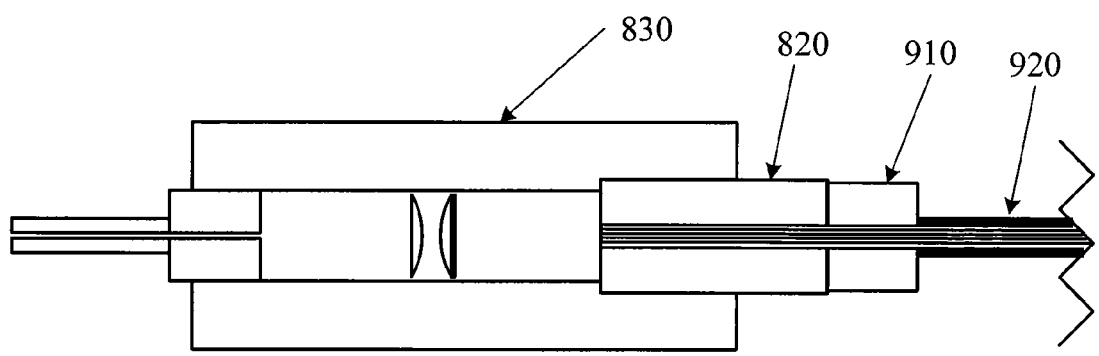
FIG. 10 illustrates a connection between the laser probe of FIG. 9 and the coupling arrangement of FIG. 8.

FIGS. 8-10 depict a fiber coupling arrangement according to the principles of the present invention. FIG. 8 shows a coupling. The optics are located in a housing 830 that connects the laser console to a disposable laser probe. In FIG. 8, the optics (in this case, lens 130 and lens with diffractive grating 210—although other optics may be used) are located in housing 830. A male connector 810 is located on one end of housing 830, and a female connector 820 is located on the other end of housing 830. In one embodiment, the connectors are standard SMA connectors, though other types of connectors may be employed.

FIG. 9 is a partial view of a laser probe according to the principles of the present invention. A disposable multispot laser probe includes a male connector 910, a sheath 920 that carries one or more optical fibers, a hand piece 930, and a cannula 940 that terminates in three optical fibers 220, 230, 240 (each with a bent tip).

FIG. 10 illustrates a connection between the laser probe of FIG. 9 and the connector arrangement of FIG. 8. In FIG. 10, male connector 910 is engaged with female connector 820, thus coupling the laser probe with the laser source. Optics enclosed in housing 830 diffract the incident beam into multiple beams that are carried by optical fibers 220, 230, 240.

FIGS. 11 and 12 are end views of a connector arrangement according to the principles of the present invention. FIG. 11 is an end view of the female connector and FIG. 12 is an end view of the male connector. A spring ball 1110 engages slot 1210 and properly aligns the optical fibers (depicted as small circles). Other mechanical alignment features, such as slots and mating protrusions, may be employed to align the optical fibers.

FIG. 13 is a cross section view of a laser probe. In FIG. 13, the laser probe has PVC sheathing 1310, a handpiece 1320, an optical fiber 1330, and a cannula 1340. A laser beam is emitted from the distal end of fiber 1330.

Figure 14:
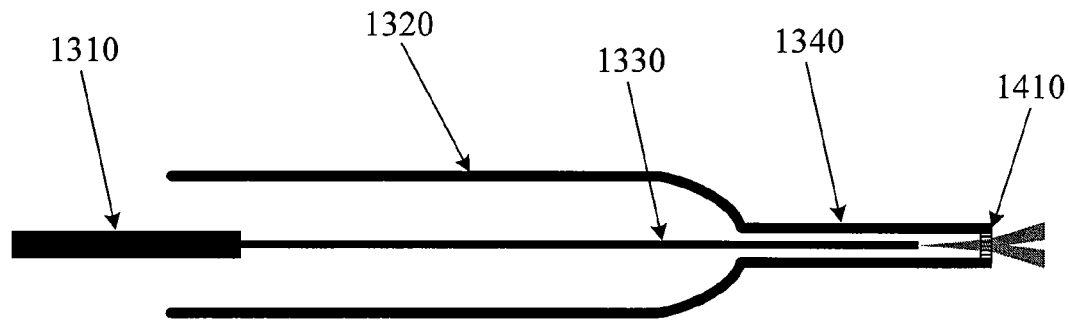
FIG. 14 is a cross section view of a laser probe with a diffractive grating according to the principles of the present invention.

FIG. 14 is a cross section view of a laser probe with a diffractive grating according to the principles of the present invention. In FIG. 14, diffractive grating 1410 is fitted onto the end of cannula 1340. Optical fiber 1330 terminates inside cannula 1340 ahead of diffractive grating 1340. In this manner, a laser beam emitted by optical fiber 130 passes through diffractive grating 1410. As previously discussed, diffractive grating 1410 produces multiple diffracted beam spots. In FIG. 14, two diffracted beams are shown, but in other embodiments of the present invention, any number of diffracted beams may be produced as the incident beam passes through diffractive grating 1410. In various embodiments of the present invention, a surface grating, volume hologram, or a combination of both may be employed as discussed above. In other embodiments, diffractive grating 1410 may be designed to produce different spot patterns as previously discussed.

Figure 15:
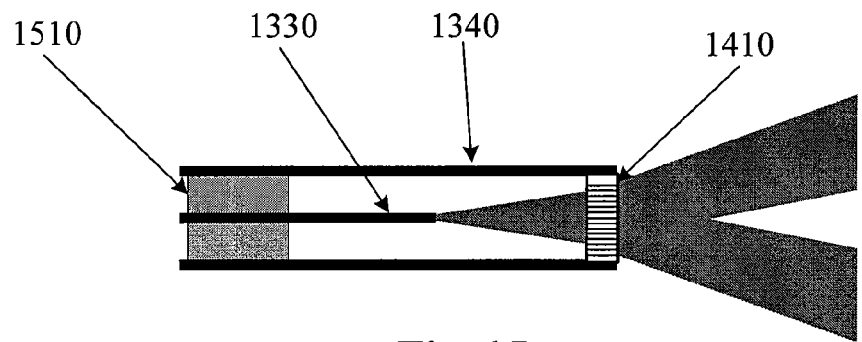
FIG. 15 is an exploded cross section view of the distal tip of the laser probe of FIG. 14.

FIG. 15 is an exploded cross section view of the distal tip of the laser probe of FIG. 14. This drawing more clearly shows the arrangement of the components and the path of the beams.

FIG. 15 also includes a centering cylinder 1510 that is designed to center optical fiber 1330 in cannula 1340. The distal end of optical fiber 1330 is positioned a distance from diffractive grating 1410 so that the beam emitted by optical fiber 1330 can expand to fill diffractive grating 1410 as shown. Diffractive grating 1410 diffracts the beam into multiple directions so that a multitude of virtual images appear in the plane of the emitting fiber.

Figure 16:
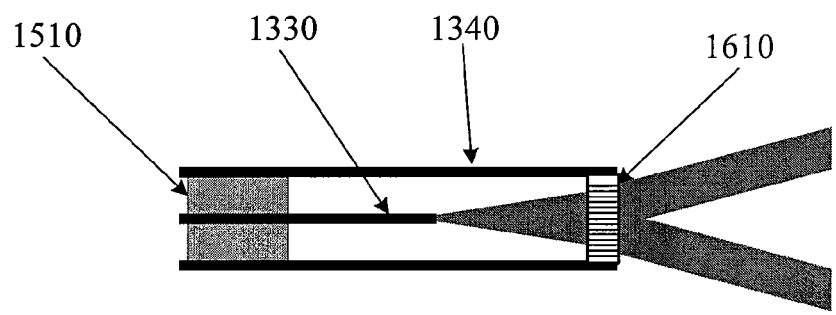
FIG. 16 is an exploded cross section view of the distal tip of a laser probe in which optical power is incorporated into the diffractive grating.

FIG. 16 is an exploded cross section view of the distal tip of a laser probe in which optical power is incorporated into diffractive grating 1610. Diffractive grating 1610 is designed to focus the diffracted beams. For example, diffractive grating may be designed to emit a multitude of collimated diffracted beams. Collimated diffracted beams result in a more concentrated spot pattern on the retina. In other embodiments, diffractive grating 1610 is designed to generate converging diffracted beams.

From the above, it may be appreciated that the present invention provides an improved system for photocoagulation of the retina. Utilizing a diffractive grating or assembly, a single incident laser beam can be diffracted into a spot pattern suitable for photocoagulating retinal blood vessels. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A laser probe comprising:
   an emitting optical fiber for emitting a beam of light;
   optics located on the emitting side of the emitting optical fiber, the optics comprising a diffractive surface for diffracting the beam of light emitted by the emitting optical fiber such that the beam of light emitted by the emitting optical fiber is diffracted into two or more diffracted beams of light, each of the two or more diffracted beams of light focused in a plane generally parallel to the diffractive surface; and
   two or more receiving optical fibers, each of the two or more receiving optical fibers located opposite the emitting optical fiber, receiving ends of each of the two or more receiving optical fibers located in the plane generally parallel to the diffractive surface, each of the two or more receiving optical fibers for receiving a beam of light diffracted by the optics.

2. The laser probe of claim 1 wherein the optics further comprise:
   a first lens; and
   a second lens located opposite the first lens, the second lens comprising a diffractive surface.

3. The laser probe of claim 2 wherein the first lens is an aspheric lens and the second lens is an aspheric lens with a diffractive surface.

4. The laser probe of claim 1 wherein the optics diffract the beam of light emitted by the emitting optical fiber into a two dimensional array of beam spots.

5. The laser probe of claim 1 wherein the optics comprise a diffractive grating.

6. The laser probe of claim 1 wherein the optics comprise a hybrid surface grating/volume hologram multiplex grating assembly.

7. The laser probe of claim 6 wherein the grating assembly further comprises:

a generally circular surface grating section located in a center of the grating assembly, the surface grating section for diffracting an incident beam at a lower bend angle; and a generally ring-like volume hologram section located around a periphery of the surface grating section, the volume hologram section for diffracting an incident beam at a higher bend angle.

8. The laser probe of claim 1 in which at least one of the two or more receiving optical fibers has a bent distal end.

9. The laser probe of claim 1 wherein the two or more receiving optical fibers are located such that each of the two or more receiving optical fibers is coupled to a single light beam diffracted by the optics.

10. The laser probe of claim 1 further comprising:
a housing at least partially enclosing the two or more receiving optical fibers.

11. A coupling for a laser probe comprising:
a housing;
optics located in the housing, the optics comprising a diffractive surface for diffracting a beam of incident light such that the beam of incident light is diffracted into two or more diffracted beams of light, each of the two or more diffracted beams of light focused in a plane generally parallel to the diffractive surface;
a first connector located on one side of the optics; and
a second connector located on the other side of the optics.

12. The coupling of claim 11 wherein the optics further comprise:
a first lens; and
a second lens located opposite the first lens, the second lens comprising a diffractive surface.

13. The coupling of claim 12 wherein the first lens is an aspheric lens and the second lens is an aspheric lens with a diffractive surface.

14. The coupling of claim 11 wherein the optics diffract the beam of light emitted by the emitting optical fiber into a two dimensional array of beam spots.

15. The coupling of claim 11 wherein the optics comprise a diffractive grating.

16. The coupling of claim 11 wherein the optics comprise a hybrid surface grating/volume hologram multiplex grating assembly.

17. The coupling of claim 16 wherein the grating assembly further comprises:
a generally circular surface grating section located in a center of the grating assembly, the surface grating section for diffracting an incident beam at a lower bend angle; and a generally ring-like volume hologram section located around a periphery of the surface grating section, the volume hologram section for diffracting an incident beam at a higher bend angle.

18. The coupling of claim 11 wherein the first and second connectors are SMA connectors.

19. The coupling of claim 11 wherein at least one of the first and second connectors comprises a mechanism for aligning optical fibers.

20. An ophthalmic laser probe comprising:
an emitting optical fiber for emitting a beam of light; and
optics located on the emitting side of the emitting optical fiber, the optics comprising a diffractive surface for at least diffracting the beam of light emitted by the emitting optical fiber into two or more diffracted beams of light such that the beam of light emitted by the emitting optical fiber is diffracted into two or more diffracted beams of light, each of the two or more diffracted beams of light focused in a plane generally parallel to the diffractive surface.

21. The laser probe of claim 20 wherein the optics comprise a diffractive grating.

22. The laser probe of claim 20 wherein the optics comprise a hybrid surface grating/volume hologram multiplex grating assembly.

23. The laser probe of claim 22 wherein the grating assembly further comprises:
a generally circular surface grating section located in a center of the grating assembly, the surface grating section for diffracting an incident beam at a lower bend angle; and
a generally ring-like volume hologram section located around a periphery of the surface grating section, the volume hologram section for diffracting an incident beam at a higher bend angle.

24. The laser probe of claim 20 wherein the optics comprise a diffractive grating with a collimating capability.

25. The laser probe of claim 20 further comprising:
a housing at least partially enclosing the emitting optical fiber.

26. The laser probe of claim 20 further comprising:
a cannula at least partially enclosing the emitting optical fiber.

27. The laser probe of claim 20 further comprising:
a centering cylinder located in the cannula, the centering cylinder for centering the emitting optical fiber in the cannula.

* * * * *